US00PP12964P2

(12) United States Plant Patent
Michalik

(10) Patent No.: US PP12,964 P2
(45) Date of Patent: Sep. 17, 2002

(54) VARIETY OF GERANIUM PLANT NAMED 'FIWOPINK'

(75) Inventor: Andrea Michalik, Dresden (DE)

(73) Assignee: Elsner pac Jungpflanzen (DE)

( * ) Notice: Subject to any disclaimer, the term of this patent is extended or adjusted under 35 U.S.C. 154(b) by 0 days.

(21) Appl. No.: 09/733,008

(22) Filed: Dec. 8, 2000

(51) Int. Cl.[7] ..... A01H 5/00

(52) U.S. Cl. ..... Plt./329

(58) Field of Search ..... Plt./325, 328, 329

*Primary Examiner*—Kent L. Bell
(74) *Attorney, Agent, or Firm*—Webb Ziesenheim Logsdon Orkin & Hanson, P.C.

(57) ABSTRACT

A new and distinct zonal geranium plant with unusual shaped red-purple colored flowers above medium green foliage. The plant is suitable for pot planting or as a bedding plant.

1 Drawing Sheet

VARIETY DENOMINATION

'Fiwopink'.

BACKGROUND OF THE INVENTION

The present invention comprises a new and distinct cultivar of *Pelargonium×hortorum* known by the varietal name 'Fiwopink'. The new variety was discovered in 1998 in a selective breeding program in Dresden, Germany. The new variety is the result of combination breeding between three unnamed, unpatented selections from breed group 7K-34-7. Plants of the new geranium differ from plants of the breeding group in lacking white at their petal bases and having a lighter pink flower color. The new variety was first asexually reproduced in 1999 by cuttings in Dresden, Germany. The new variety has been trial and field tested and has been found to retain its distinctive characteristics and remain true to type through successive propagations.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Dresden, Germany. The following observations and measurements were taken 6 months after planting rooted cuttings in 19 cm diameter pots. The color readings were taken outdoors in diffuse light during summer. Color references are primarily to The R.H.S. Colour Chart of The Royal Horticultural Society of London.

PLANT

Classification:
- *Botanical.*—*Pelargonium×hortorum.*
- *Commercial.*—Zonal geranium.

Form: Erect.
Height from media surface to top of foliage: 35–38 cm.
Height from media surface to top of umbel: 50 cm.
Width: 35 cm.

Growth: Very high degree of branching.
Strength: Does not require artificial support.
Response time: 3.5 weeks.
Leaves:
- *Width.*—10 cm.
- *Length.*—6 cm.
- *Shape.*—Reniform.
- *Margin.*—Entire; toothed.
- *Texture.*—Smooth; some pubescence.
- *Color.*—Upper surface: Green Group 138A. Lower surface: Green Group 138B.
- *Zone.*—Darker than Green Group 138A.
- *Ribs and veins.*—Color: Green Group 138D.

Petioles:
- *Color.*—Green Group 143B.
- *Length.*—3–5 cm.
- *Diameter.*—2 mm.

Stem/branches:
- *Color.*—Yellow-Green Group 144A.
- *Length.*—28 cm on average.
- *Internode length.*—3–4 cm.

THE BUD

Shape when just showing color:
- *Overall.*—Semi-spherical.
- *Individual bud.*—Narrow; elliptical.

Color: Green Group 143C.
Size when just showing color:
- *Umbel.*—7.5–9.5 cm across.
- *Individual bud.*—1–1.5 cm long; 0.7 cm wide.

INFLORESCENCE

Blooming habit: Single.
Size of fully open bloom: 4 cm wide; 4.5 cm long.
Borne: Umbel; flower on pedicel; pedicel on peduncle.
Flowers:
- *Form.*—Zygomorph.
- *Average number of inflorescences per plant in a flowering season.*—40–70.
- *Umbel* (*when flowers are open*).—Diameter: 8 cm. Depth: 4 cm.

*Number of petals*.—5.
*Size*.—Upper petals: 0.4–0.6 cm wide; 1.5 cm long. Lower petals: 0.6–1.0 cm wide; 1.5 cm long.
*Petals*.—Apex: Pointed and serrated. Base: Pointed. Margin: Entire; toothed. Color: Upper surface: Red-Purple Group 57D. Lower surface: Red-Purple Group 57D. Eye: Red-Purple Group 62C.
*Texture and appearance*.—Velvety.

Sepal:
*Quantity*.—Five.
*Length*.—11 mm.
*Width*.—2 mm.
*Apex*.—Pointed.
*Base*.—Wide.
*Margin*.—Smooth.
*Color*.—Upper surface: Yellow-Green Group 144A. Lower surface: Yellow-Green Group 144A.

Petaloids: Absent.

Pedicel:
*Length*.—2.0–2.7 cm.
*Color*.—Yellow-Green Group 144C.

Peduncle:
*Length*.—12–14 cm.
*Color*.—Yellow-Green Group 144A.

Disease/pest resistance: No susceptibility to diseases or pests has been noted to date.

Lasting quality: Long-lasting; 3–4 weeks per umbel.

REPRODUCTIVE ORGANS

Stamens:
*Anthers*.—3 mm long.
*Filaments*.—Length: 0.4 cm maximum. Color: Pink.
*Pollen*.—Orange.

Pistils:
*Number*.—One; five parted.
*Length*.—0.3–0.4 cm.
*Stigma*.—Dark pink.
*Style*.—0.8 cm long.

Ovaries:
*Color*.—Greenish.
*Length*.—0.4 cm.

Fruit: Present with 5 seeds; fruit production very weak.

GENERAL CHARACTERISTICS

1. Reniform foliage.
2. Erect, compact growth.
3. Good branching.
4. Flowers are single with unique shape.
5. Long-lasting and highly resistant against rain.
6. Low care requirements.

I claim:

1. A new and distinct variety of geranium plant substantially as shown and described.

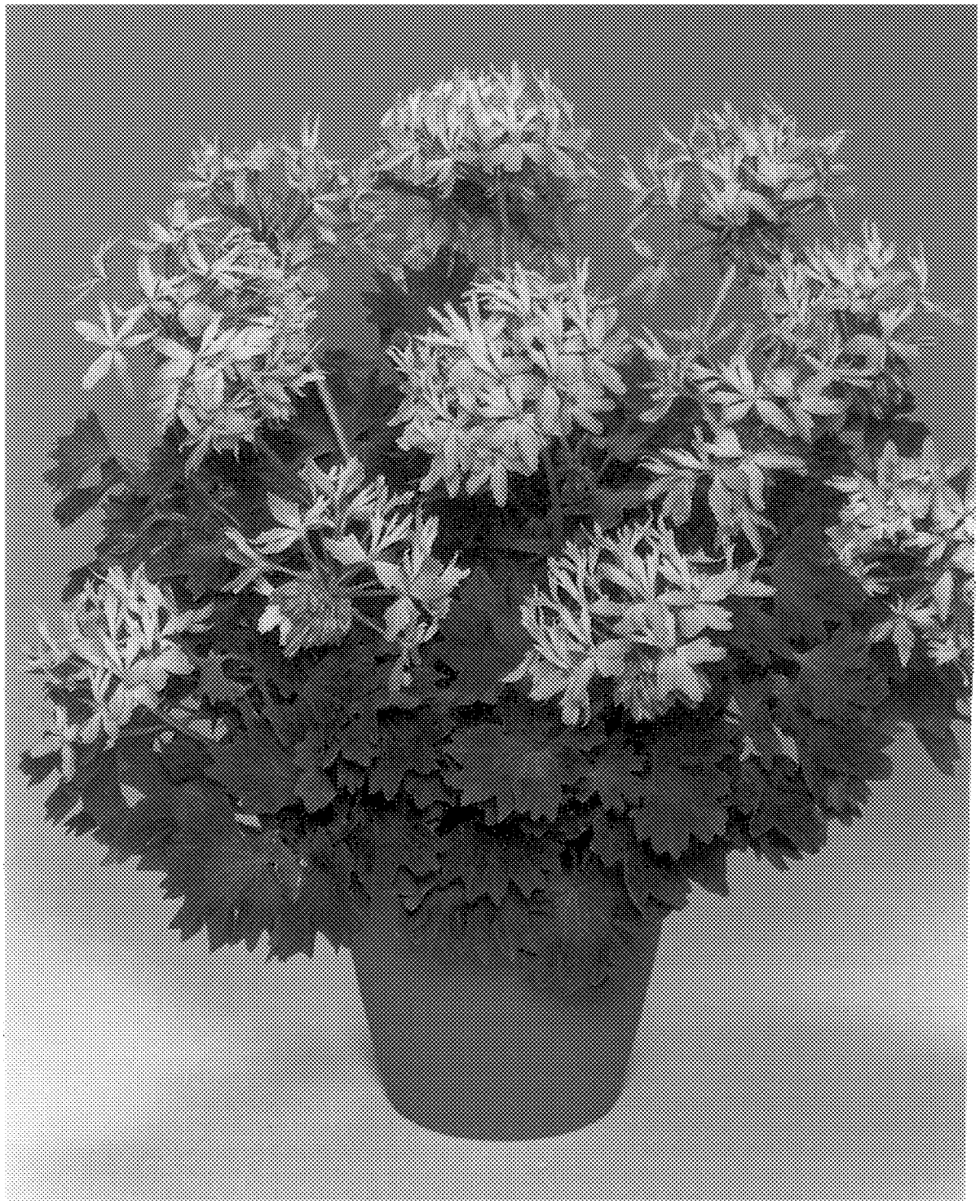

* * * * *